(12) United States Patent
Mire et al.

(10) Patent No.: US 9,486,296 B2
(45) Date of Patent: Nov. 8, 2016

(54) SURGICAL ASSEMBLY WITH FLEXIBLE ARM

(75) Inventors: David A. Mire, Cordova, TN (US); Kelli N. Sebastian, Arlington, TN (US); Paul F. Wheeler, Hernando, MS (US); David L. Fiorella, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 406 days.

(21) Appl. No.: 12/832,598

(22) Filed: Jul. 8, 2010

(65) Prior Publication Data

US 2012/0010629 A1    Jan. 12, 2012

(51) Int. Cl.
*A61B 19/00* (2006.01)
*A61B 17/02* (2006.01)
*A61B 17/29* (2006.01)

(52) U.S. Cl.
CPC .............. *A61B 90/50* (2016.02); *A61B 17/02* (2013.01); *A61B 2017/2908* (2013.01); *A61B 2090/508* (2016.02)

(58) Field of Classification Search
CPC .................... A61B 19/201; A61B 2017/2908; A61B 2017/00911; A61B 90/50; A61B 1/018
USPC ............................... 606/205, 130, 1; 604/104
See application file for complete search history.

(56) References Cited

U.S. PATENT DOCUMENTS

| | | | |
|---|---|---|---|
| 3,858,578 A | 1/1975 | Milo | |
| 4,151,840 A * | 5/1979 | Barrington | 600/40 |
| 4,353,358 A * | 10/1982 | Emerson | 600/139 |
| 5,513,827 A | 5/1996 | Michelson | |
| 5,522,788 A * | 6/1996 | Kuzmak | 600/141 |
| 5,522,827 A * | 6/1996 | Combs et al. | 606/167 |
| 5,603,723 A * | 2/1997 | Aranyi et al. | 606/205 |
| 5,632,717 A * | 5/1997 | Yoon | 600/106 |
| 5,636,815 A * | 6/1997 | Wilson | 248/125.9 |
| 5,662,300 A | 9/1997 | Michelson | |
| 5,766,196 A * | 6/1998 | Griffiths | 606/170 |
| 5,830,231 A * | 11/1998 | Geiges, Jr. | 606/205 |
| 5,899,425 A * | 5/1999 | Corey Jr. et al. | 248/276.1 |
| 6,439,429 B1 * | 8/2002 | Gross | 222/92 |
| 6,439,439 B1 * | 8/2002 | Rickard et al. | 222/391 |
| 6,461,363 B1 * | 10/2002 | Gadberry et al. | 606/139 |
| 6,464,629 B1 | 10/2002 | Boone et al. | |
| 6,688,564 B2 | 2/2004 | Salvermoser et al. | |
| 6,758,808 B2 * | 7/2004 | Paul et al. | 600/229 |
| 6,767,153 B1 | 7/2004 | Holbrook | |
| 6,860,668 B2 | 3/2005 | Ibrahim et al. | |
| 2001/0025905 A1 | 10/2001 | Carpenter et al. | |
| 2003/0036748 A1* | 2/2003 | Cooper et al. | 606/1 |
| 2003/0083596 A1* | 5/2003 | Kramer et al. | 600/595 |
| 2003/0089831 A1 | 5/2003 | Salvermoser et al. | |
| 2003/0165352 A1 | 9/2003 | Ibrahim et al. | |
| 2003/0216619 A1 | 11/2003 | Scirica et al. | |
| 2004/0138525 A1* | 7/2004 | Saadat et al. | 600/104 |
| 2004/0242969 A1* | 12/2004 | Sherts et al. | 600/231 |

(Continued)

*Primary Examiner* — Richard Louis

(57) ABSTRACT

A surgical assembly includes a tensioner having a first end and a second end. A tension member extends from the first end of the tensioner. A mounting member is connected to the second end of the tensioner. An arm extends from the first end of the tensioner and includes a series of relatively moveable links that define an axial bore configured for disposal of the tension member. Each link defines a first mating surface and a second mating surface disposed in a configuration such that tensioning of the tension member interlocks the first mating surface with the second mating surface of an adjacent link in the series to selectively fix the links in a selected orientation.

20 Claims, 7 Drawing Sheets

(56) References Cited

U.S. PATENT DOCUMENTS

| | | | |
|---|---|---|---|
| 2005/0070764 A1* | 3/2005 | Nobis et al. | 600/131 |
| 2005/0131457 A1 | 6/2005 | Douglas et al. | |
| 2005/0152739 A1 | 7/2005 | Ibrahim et al. | |
| 2005/0197536 A1* | 9/2005 | Banik et al. | 600/179 |
| 2005/0226682 A1 | 10/2005 | Chersky et al. | |
| 2005/0250990 A1* | 11/2005 | Le et al. | 600/114 |
| 2006/0084831 A1* | 4/2006 | Zhang | 585/670 |
| 2006/0094931 A1* | 5/2006 | Danitz et al. | 600/141 |
| 2008/0121765 A1* | 5/2008 | Fetzer | 248/122.1 |
| 2008/0243106 A1* | 10/2008 | Coe et al. | 606/1 |
| 2009/0228007 A1* | 9/2009 | Justin et al. | 606/62 |

* cited by examiner

SURGICAL ASSEMBLY WITH FLEXIBLE ARM

TECHNICAL FIELD

The present disclosure generally relates to medical devices, systems and methods employed during surgical applications, and more particularly, to a surgical assembly that includes a series of interlocking links configured to support a surgical instrument, which is used, for example, with a minimally invasive surgical procedure.

BACKGROUND

Invasive surgical procedures such as open surgery for pathologies located within the body can cause significant trauma to intervening tissues. These procedures often require that the skin, tissue and/or vessels surrounding a surgical site be cut, removed, and/or repositioned so that a surgeon can access the site within the body. This trauma to the body may result in damage and scarring, as well as infection and long recovery.

Percutaneous minimally invasive surgical procedures are known that have attempted to overcome the above drawbacks of open surgery. Minimally invasive surgical procedures minimize disruption and trauma to the body to reduce recovery time and post-operative pain. For example, minimally invasive surgical techniques are employed for spinal and neurosurgical applications to access surgical sites within the body adjacent vital intervening tissues, in an effort to avoid damaging such vital tissues. Surgical retractors, mounting assemblies and other instruments are used in such minimally invasive procedures to increase the workspace of the minimally invasive surgical incision and adjacent areas used to access a surgical site. This disclosure describes an improvement over these prior art technologies.

SUMMARY OF THE INVENTION

Accordingly, a surgical assembly, system and related methods are provided for employment during surgical applications. It is contemplated that the surgical assembly includes a series of interlocking links configured to support a surgical instrument and is used, for example, with a minimally invasive surgical procedure.

In one particular embodiment, in accordance with the principles of the present disclosure, a surgical assembly is provided. The surgical assembly includes a tensioner having a first end and a second end. A tension member extends from the first end of the tensioner. A mounting member is connected to the second end of the tensioner. An arm extends from the first end of the tensioner and includes a series of relatively moveable links that define an axial bore configured for disposal of the tension member. Each link defines a first mating surface and a second mating surface disposed in a configuration such that tensioning of the tension member interlocks the first mating surface with the second mating surface of an adjacent link in the series to selectively fix the links in a selected orientation.

In one embodiment, the surgical assembly includes a tensioner having a first end, a second end and a body. The second end includes a slide connected with the body. A cable is connected with the body and extends from the first end of the tensioner. A mounting member is connected with the body of the tensioner. An arm includes a series of relatively movable links that define an axial bore configured for disposal of the cable. Each link further defines a first mating surface and an opposing second mating surface. The mating surfaces include interlocking teeth disposed in a configuration such that engagement of the slide relative to the body selectively tensions the cable via engagement of the links and the first mating surface interlocks with the second mating surface of an adjacent link in the series to selectively fix the links in a selected orientation.

In one embodiment, the surgical assembly includes a pistol-grip tensioner having a body. A slide is connected to the body. A ratchet mechanism is connected to the body with the slide. A cable is connected with the body. A mounting member is connected with the body. A proximal link has a first end including a mating surface and a second end mounted with the body. A series of relatively movable links define an axial bore configured for disposal of the cable. Each link further defines a first mating surface and a second mating surface. Each link is movable relative to an adjacent link through an angular range in a single plane only. The mating surface of the proximal link is configured to interlock with the first mating surface. A distal link has a mating surface configured to interlock with the second mating surface and an end for releasably engaging an instrument. Engagement of the slide relative to the body selectively tensions the cable via engagement of the links and the first mating surface interlocks with the second mating surface of an adjacent link in the series to selectively fix the links in a selected orientation via fixation of the ratchet mechanism with the body.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

Figure 1:
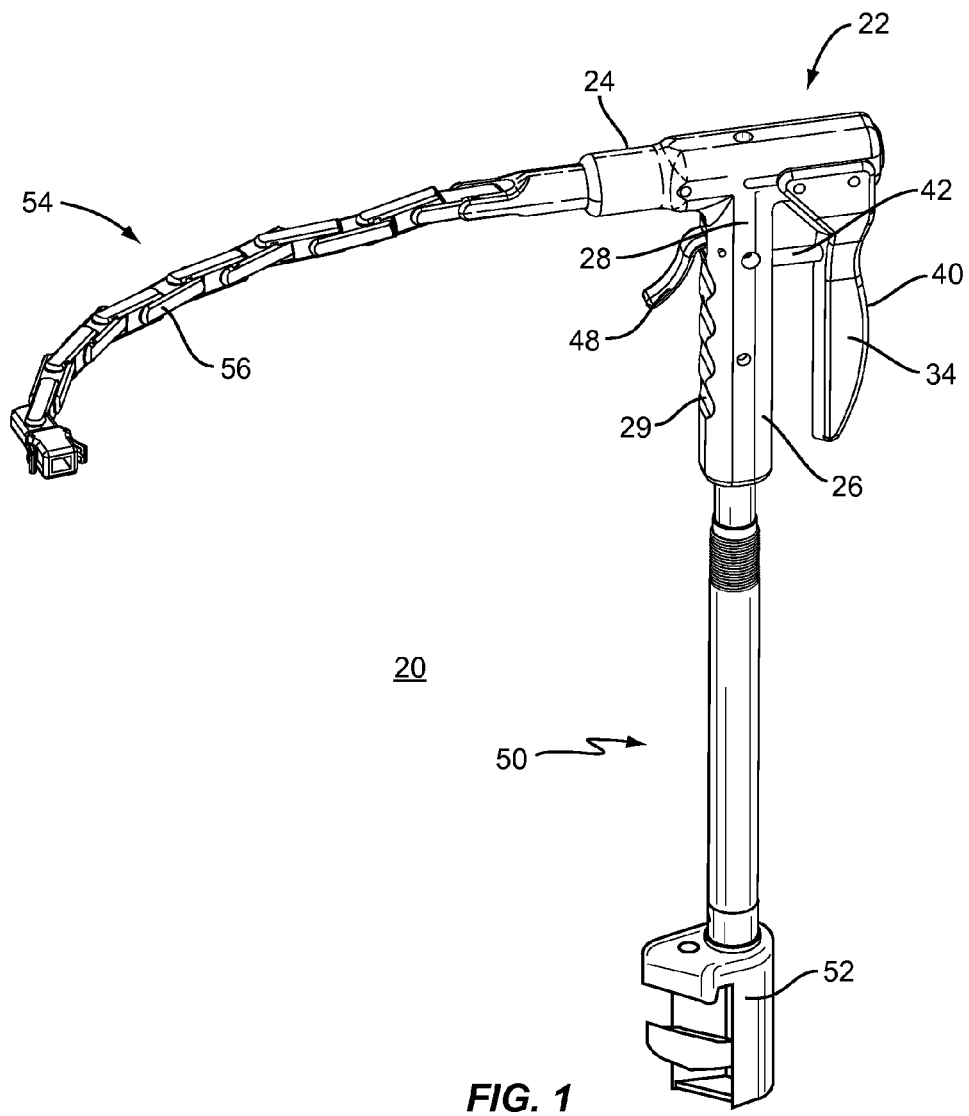
FIG. 1 is a perspective view of one particular embodiment of a surgical assembly in accordance with the principles of the present disclosure.
Figure 2:
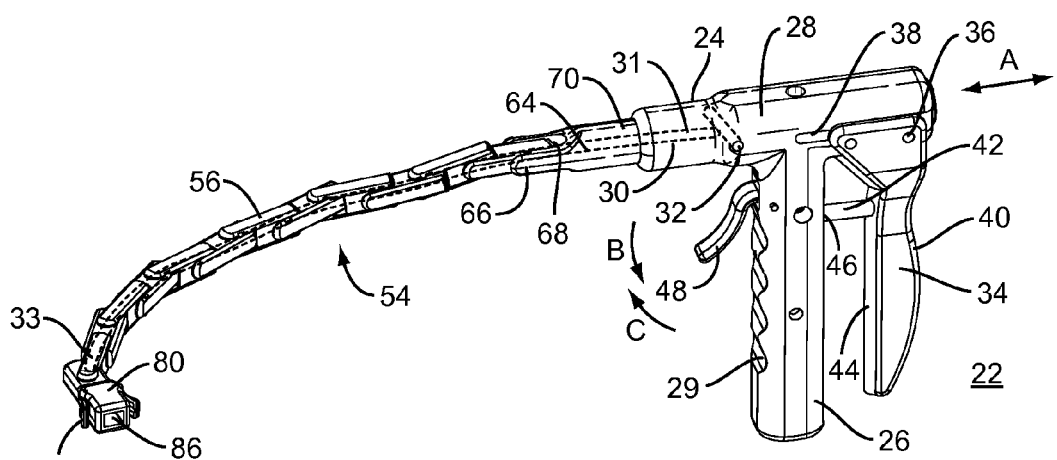
FIG. 2 is a perspective view of a tensioner and an arm of the surgical assembly shown in FIG. 1.
Figure 3:
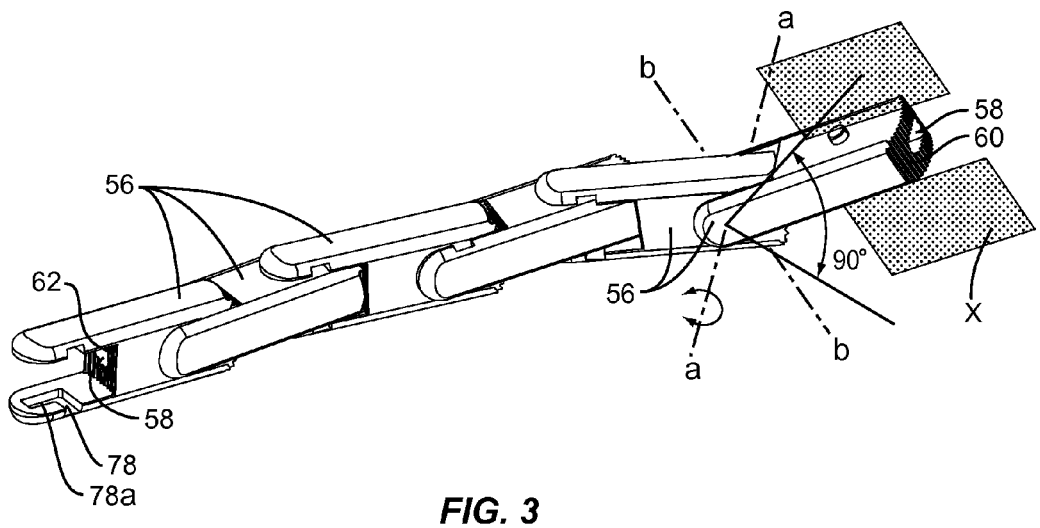
FIG. 3 is an enlarged perspective view of links shown in FIG. 1.
Figure 4:
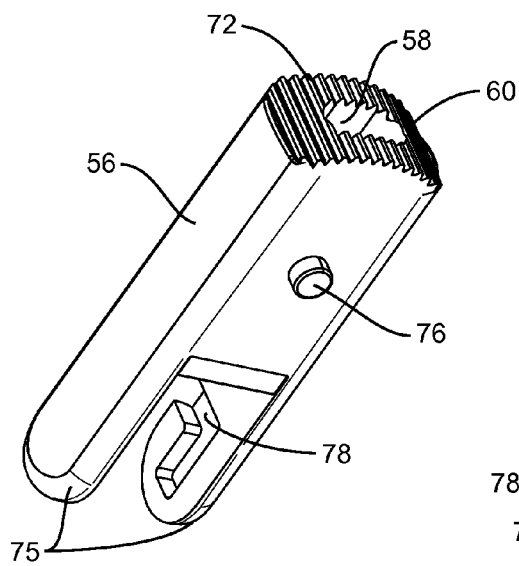
FIG. 4 is an enlarged perspective view of a link shown in FIG. 1.
Figure 5:
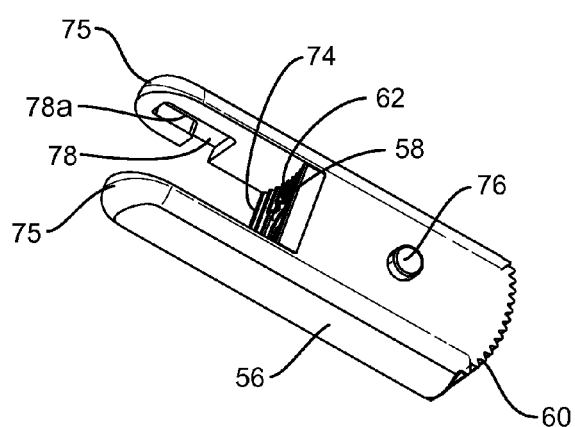
FIG. 5 is an enlarged perspective view of a link shown in FIG. 1.
Figure 6:
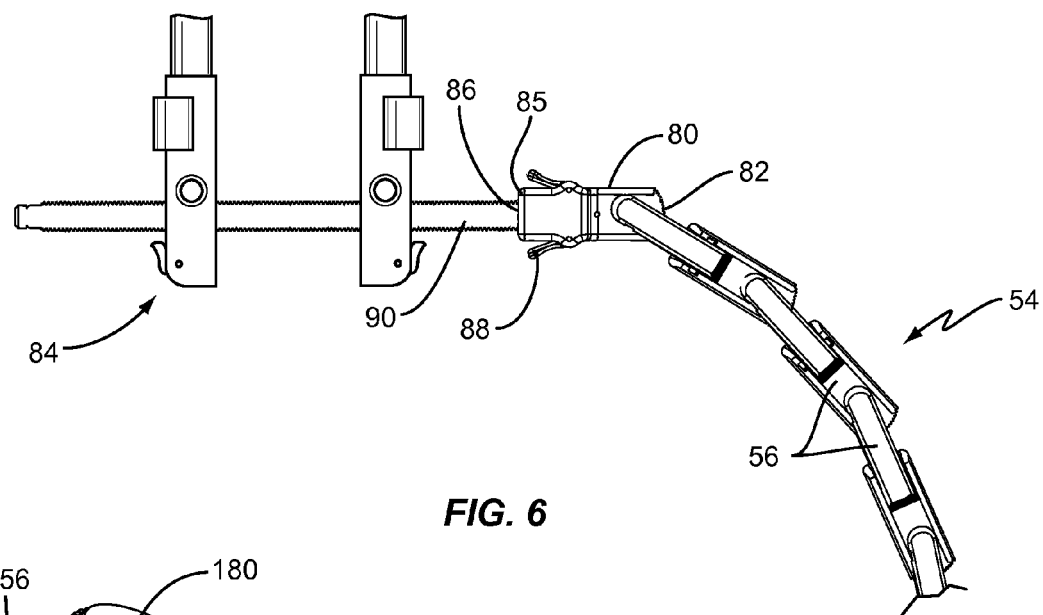
FIG. 6 is a cutaway top view of the surgical assembly shown in FIG. 1 connected to an instrument.
Figure 7:
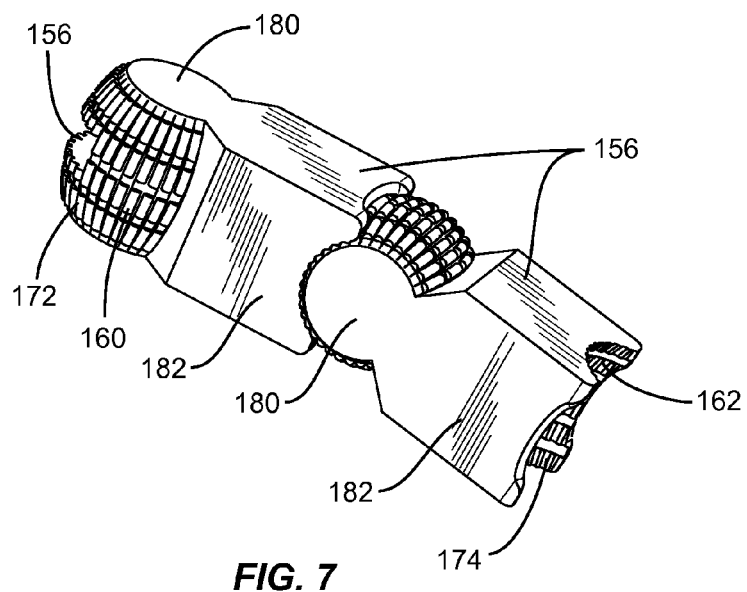
FIG. 7 is a perspective view of one embodiment of the links shown in FIG. 3.
Figure 8:
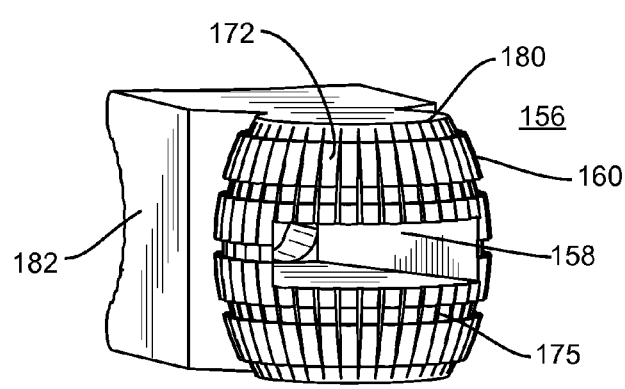
FIG. 8 is an enlarged perspective view of a link shown in FIG. 7.
Figure 9:
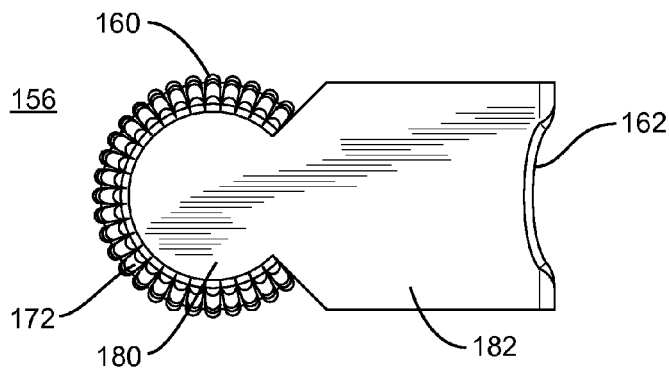
FIG. 9 is an enlarged plan view of the link shown in FIG. 7.
Figure 10:
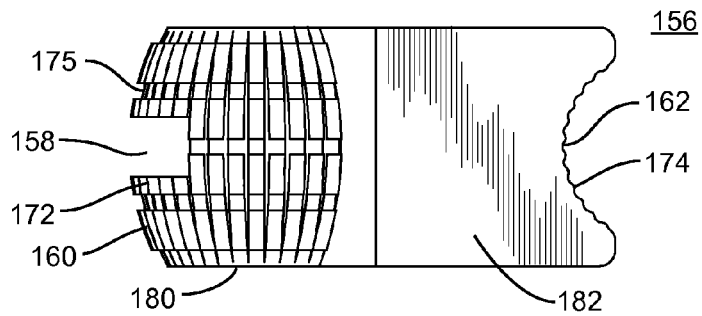
FIG. 10 is an enlarged side view of the link shown in FIG. 7.
Figure 11:
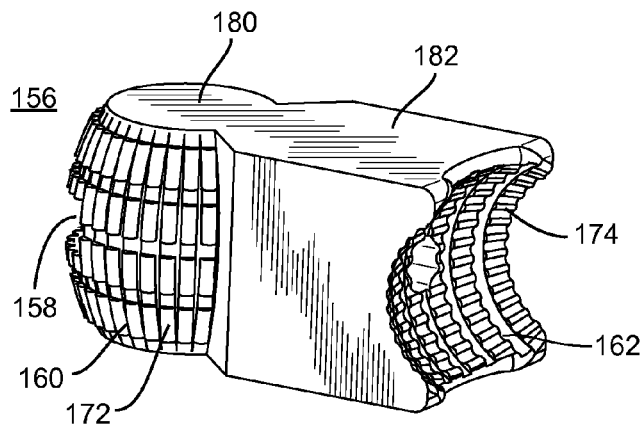
FIG. 11 is a perspective view of the link shown in FIG. 7.
Figure 12:
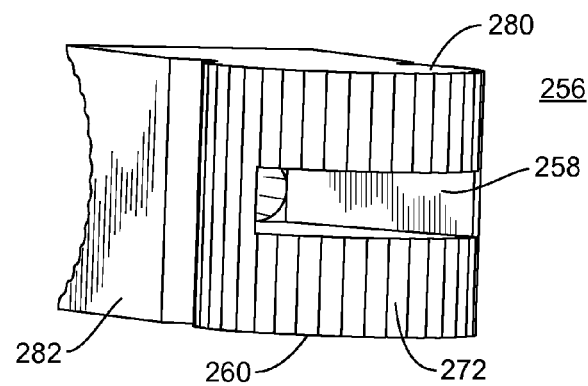
FIG. 12 is a perspective view of one embodiment of the link shown in FIG. 4.
Figure 13:
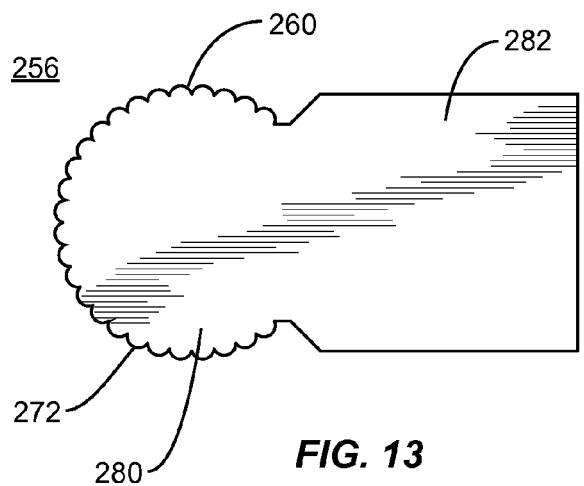
FIG. 13 is a plan view of the link shown in FIG. 12.
Figure 14:
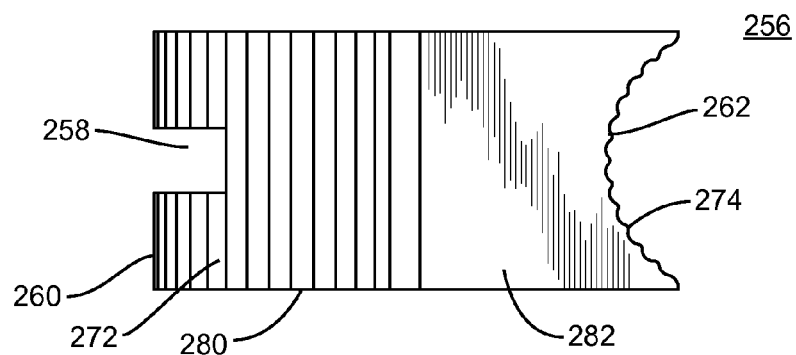
FIG. 14 is a side view of the link shown in FIG. 12.
Figure 15:
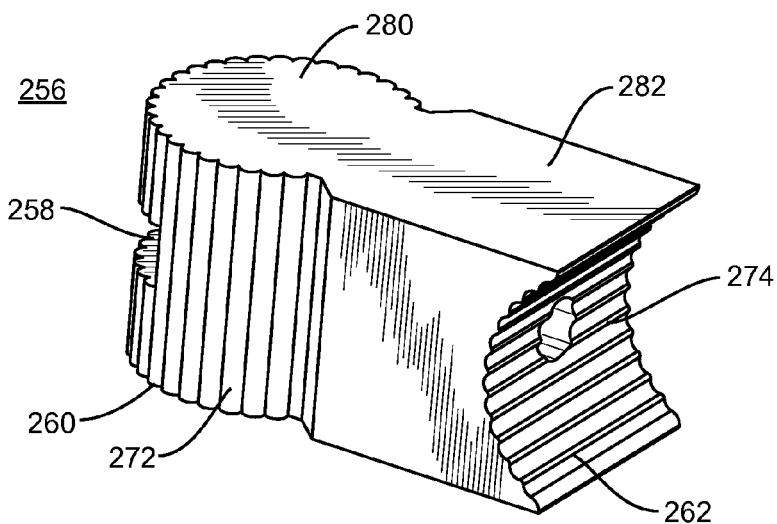
FIG. 15 is a perspective view of the link shown in FIG. 12.

The exemplary embodiments of the surgical assembly, related systems and methods of use disclosed are discussed in terms of medical devices employed during surgical applications and more particularly, in terms of a surgical assembly that includes a series of interlocking links configured to support a surgical instrument, which is used, for example, with a minimally invasive surgical procedure. It is envisioned that the surgical assembly, systems and methods of use disclosed provide a reliable and user-friendly mount and positioning assembly with an interlocking geometry of links, which is low profile to a patient allowing a surgeon facile access to a surgical site. It is further envisioned that the surgical assembly is adjustable without requiring the use of several knob/button devices.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical assembly may be employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may be employed with procedures for treating the lumbar, cervical, thoracic and pelvic regions of a spinal column. The system and methods of the present disclosure may also be used on animals, bone models and other non-living substrates, such as for training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The following discussion includes a description of a surgical assembly, related components and exemplary methods of employing the surgical assembly in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there is illustrated components of a surgical assembly 20 in accordance with the principles of the present disclosure.

The components of surgical assembly 20 and related systems are fabricated from materials suitable for medical applications, including metals, polymers, ceramics, biocompatible materials and/or their composites, depending on the particular application and/or preference of a medical practitioner. For example, the components of the surgical assembly, individually or collectively, can be fabricated from materials such as stainless steel, titanium, thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, biocompatible materials such as polymers including plastics, metals, ceramics and composites thereof, rigid polymers including polyphenylene, polyamide, polyimide, polyetherimide, polyethylene, epoxy, and various components of the surgical assembly may have material composites, including the above materials, to achieve various desired characteristics such as strength, rigidity, elasticity, compliance, biomechanical performance, durability and radiolucency or imaging preference.

Surgical assembly 20 includes a tensioner 22 having a first end 24, a second end 26 and a body 28. Body 28 has a pistol grip configuration and second end 26 defines finger grips 29 to facilitate handling and manipulation of tensioner 22 by a practitioner. It is contemplated that tensioner 22 may be monolithically formed or integrally assembled. Body 28 has a cylindrical configuration and defines an interior cavity for support of various components, as will be described.

A tension member, such as, for example, a cable 30 extends from first end 24. Cable 30 has a first end 31 attached to a pin 32 of body 28 and extends therefrom to a distal end 33 through the interlocking links. Cable 30 is elastic and has a tension, which can be increased or decreased to facilitate support and positioning of a surgical instrument(s). It is envisioned that cable 30 has a band configuration. It is further envisioned that cable 30 may have other configurations, such as, for example, a wire rope with a twisted helix.

Tensioner 22 includes a first member, such as, for example, a slide 34 that is relatively movable from body 28. Slide 34 is connected to body 28 with pins 36 that extend into body 28 through slots 38, which are disposed on opposing sides of body 28. Slide 34 has a handle grip configuration and is designed for manipulation for tensioning cable 30. Slide 34 has a user contoured surface 40 that upon engagement causes axial movement of slide 34, in the direction shown by arrows A in FIG. 2, as facilitated by movement of pins 36 along slot 38.

Slide 34 includes an internal member extending axially along the interior cavity of body 28 to engage a proximal end of the interlocking links. As the internal member of slide 34 engages the proximal end of the interlocking links, the proximal end of the interlocking links are urged/forced in the direction of arrows A according to the manipulation of slide 34. This engagement increases or decreases, depending on the direction of manipulation and/or the magnitude of force applied to slide 34 along arrows A, the tension of cable 30 due to the connection of cable 30 with body 28 and distal end 33 of the interlocking links, as will be described. As tension is applied to proximal end 31 relative to the proximal end of the links, the distal end of the links is pulled towards the proximal link forcing the links together. It is envisioned that tensioner 22 may include alternative first members to tension cable 30, such as, for example, a side projecting slide bolt.

Slide 34 is releasably locked to a fixed position with body 28 via a ratchet mechanism 42. Ratchet mechanism 42 extends from a front surface 44 of slide 34 and passes through a slot 46 of body 28. Body 28 is selectively fixable with ratchet mechanism 42 during relative movement of slide 34. Ratchet mechanism 42 is a rack with serrations that engage or mesh with reciprocal grooves in slot 46 to selectively fix the tension of cable 30. As slide 34 moves in the direction of arrows A, the tension of cable 30 is increased or decreased. Upon movement of slide 34 to a selected tension of cable 30, body 28 is selectively fixed with ratchet mechanism 42.

Tensioner 22 includes a second member, such as, for example, a trigger 48 that is engageable to selectively fix body 28 with ratchet mechanism 42 at a selected tension of cable 30. Trigger 48 can be manipulated, in the direction shown by arrow C in FIG. 2, to lock ratchet mechanism 42 with slot 46 at a selected tension of cable 30. Trigger 48 is pivotable relative to body 28 and is depressed, in the direction shown by arrow B in FIG. 2, to disengage ratchet mechanism 42 from slot 46 and release cable 30 from the selected tension. It is contemplated that tension of cable 30 may be selectively fixed via free manipulation, and not require a locking element. It is further contemplated that a first tension of cable 30 may be selected and locked, and then released from that tension and a second tension selected and locked such that the tension of cable 30 can be adjusted during a surgical procedure. Cable 30 may be adjusted to one or a plurality of tensions during a surgical procedure.

A mounting member 50 is connected to second end 26. Mounting member 50 has an adjustable clamp 52 configured for mounting with a fixture, such as, for example, a bed rail (not shown). It is contemplated that mounting can be performed from a sterile field after a patient has been draped.

An arm 54 extends from first end 24 and includes a series of relatively movable links 56 that define an axial bore 58 configured for disposal of cable 30. Axial bore 58 has an oval cross section configuration. It is envisioned that bore 58 may have alternative cross section geometries, such as, for example, circular, polygonal, uniform, non-uniform and/or alternate or changing diameter. Each link 56 defines a first mating surface 60 and an opposing second mating surface 62, the mating surfaces being configured to interlock with a reciprocal mating surface of an adjacent link 56 in the series of links for support and positioning of an instrument, as will be described. Axial bore 58 extends through mating surfaces 60,62 for disposal of cable 30. It is contemplated that cable 30 is threaded with links 56.

A proximal link 64 has a first end 66 including a mating surface 68 configured to interlock, similar to that described herein, with first mating surface 60 and a second end 70 mounted with first end 24. First end 66 also connects to link 56 via a pin/slot attachment for relative rotation of the links prior to fixation, as described below.

Cable 30 extends from pin 32 through proximal link 64 and into links 56. Second end 70 is engageable with the internal member of slide 34 and proximal link 64 is movable and connected with the series of links 56, as described above, to tension cable 30. It is contemplated that proximal link 64 is axially movable and rotatable relative to first end 24 of body 28 to facilitate positioning of the instrument. It is further contemplated that proximal link 64 may be non-rotatable.

Mating surface 60 includes a plurality of teeth 72 and adjacent grooves that interlock with a plurality of teeth 74 and adjacent grooves of mating surface 62. As slide 34 is manipulated or squeezed relative to body 28, the internal member of slide 34 engages proximal link 64 such that interlocking teeth 72,74 mesh and become disposed in a configuration to selectively tension cable 30 via engagement of links 56, which tighten. As the tension of cable 30 is increased, first mating surface 60 interlocks with second mating surface 62 of an adjacent link 56 in the series to selectively fix links 56 in a selected orientation.

Teeth 72, 74 become disposed in the grooves of the opposing mating surface to selectively fix a link 56 and an adjacent link 56 in a particular relative orientation such that arm 54 and surgical assembly 20 support an instrument in a position relative to a surgical site, according to the requirements of a particular application. It is envisioned that surgical assembly 20 may position an instrument in one or a plurality of orientations relative to a surgical site, and that arm 54 can be flexed in a plurality of orientations such as, multi-axial, linear, arcuate, helical and perpendicular and then fixed for orientation of an instrument. It is envisioned that the mating surfaces may be knurled, textured, form a friction or pressure fit engagement, notch and groove, single tooth and groove and/or include separate mechanical fixation such as a clamp. Upon interlocking fixation, it is envisioned that links 56 are configured to prevent undesired rotation of link joints and twisting of cable 30.

Mating surface 60 has a convex configuration and mating surface 62 has a concave configuration to facilitate interlocking fixation of surfaces 60,62. Each link 56 includes extensions 75 configured to support an adjacent link 56. Each link 56 has a pin 76 configured for receipt within a slot 78 formed in extensions 75 of an adjacent link 56. Disposal of pin 76 within slot 78 facilitates attachment of links 56 and hinged movement such that links 56 are relatively rotatable and/or pivotable, as will be described, for fixation of arm 54 in a preselected orientation. Slot 78 includes an axial channel 78a that is configured for movement of pin 76 therein. During flexing of arm 54, pin 76 is freely movable within channel 78a. As slide 34 is manipulated to tension cable 30 and fix links 56 in a selected orientation, links 56 tighten and pin 76 is drawn deeper into channel 78a for fixation. Upon release of tension on cable 30, as described above, pin 76 can again freely move in channel 78a.

Prior to interlocking fixation, link 56 is movable relative to an adjacent link 56 through an angle in a single plane only to provide reliability in operation and fixation of mating parts. Mating surface 60 is elongated along a first axis, such as, for example, axis a and a first mating surface 60 of an adjacent link 56 is elongated along a second axis, such as, for example, axis b. Axis a is oriented transverse to axis b. Each link 56 is movable relative to an adjacent link 56 through an angular range in a single plane only, such as, for example, a plane x. It is contemplated that each link 56 is movable relative to an adjacent link 56 through an angular range of 90 degrees. It is contemplated that links 56 may alternatively be relatively movable in one or a plurality of planes, directions and/or degrees of freedom, may be rotatable or twisted and/or axially movable.

A distal link 80 has a mating surface 82 configured to interlock, similar to that described herein, with second mating surface 62 and an end 85 for releasably engaging an instrument, such as, for example, a retractor assembly 84.

End 85 defines a cavity 86 for receiving retractor assembly 84 and a pair of pawls 88 for releasably retaining retractor assembly 84 within cavity 86. Retractor assembly 84 includes a bar 90 having grooves (not shown) that are inserted within cavity 86. For connection of retractor assembly 84 with surgical assembly 20, bar 90 is inserted within cavity 86, which causes pawls 88 to become disposed within the grooves such that distal link 80 releasably retains retractor assembly 84. To disengage retractor assembly 84 from surgical assembly 20, pawls 88 are engaged inwardly to cause a portion of pawls 88 to pivot outwardly such that pawls 88 are released from the grooves such that bar 90 is removable from cavity 86.

In assembly, operation and use, the surgical system including surgical assembly 20 is employed, for example, with a minimally invasive surgical procedure for spinal and neurosurgical applications with a patient. For example, during minimally invasive spine surgery, a surgeon will make a small incision, typically less than one inch, in the skin of a patient's back over vertebrae to be treated. One or more dilators may be employed to gradually separate the muscles and create a portal through which the surgery may be performed.

Mounting member 50 of surgical assembly 20 is mounted to a bed rail, or other fixture. Retractor assembly 84 is attached to arm 54, as described above, and surgical assembly 20 with retractor assembly 84 is positioned adjacent the surgical site over the small incision described above. As facilitated by the configuration of surgical assembly 20, retractor assembly 84 may be positioned, repositioned and/or adjusted, to one or a plurality of orientations.

It is envisioned that the use of microsurgical and image guided technologies may be employed to access, view and repair spinal deterioration or damage, with the aid of surgical assembly 20. Upon completion of the procedure, the surgical instruments and assemblies are removed and the incision is closed. Alternatively, surgical assembly 20 may employed with an open spine surgery, which may involve making a long incision down the back, stripping large bands of muscle away from the spine and using retractor assembly 84 to retract, or pull the surrounding tissues and muscles to create a surgical site for treatment. It is envisioned that surgical assembly 20 may also be employed with mini-open surgery and percutaneous surgical implantation.

It is contemplated that a surgical procedure may employ other instruments that can be mounted with surgical assembly 20, such as, for example, nerve root retractors, tissue retractors, forceps, cutter, drills, scrapers, reamers, separators, rongeurs, taps, cauterization instruments, irrigation and/or aspiration instruments, illumination instruments and/or inserter instruments.

Surgical assembly 20 may be employed for performing spinal surgeries, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

In one embodiment, as shown in FIGS. 7-11, arm 54 of surgical assembly 20, similar to that described above, includes a series of relatively movable links 156. Link 156 has a first end 180 having a barrel configuration and a second end 182 having a block configuration. Links 156 define an axial bore 158 configured for disposal of cable 30. Axial bore 158 is formed with each link 156 and has a rectangular configuration therethrough that decreases in width from first end 180 to second end 182. First end 180 defines a first mating surface 160 and second end 182 defines an opposing second mating surface 162, the mating surfaces being configured to interlock with a reciprocal mating surface of an adjacent link 156 in the series of links for support and positioning of an instrument, as described above. Axial bore 158 extends through mating surfaces 160,162 for disposal of cable 30.

Mating surfaces 160,162 include a plurality of teeth 172,174 and adjacent grooves disposed arcuately about the barrel surface that interlock, similar to that described above. Teeth 172, 174 are disposed in parallel rows about mating surfaces 160,162, and are spaced apart by channels 175. As the tension of cable 30 is increased, first mating surface 160 interlocks with second mating surface 162 of an adjacent link 156 in the series to selectively fix links 156 in a selected orientation. Teeth 172, 174 become disposed in the grooves of the opposing mating surface to selectively fix a link 156 and an adjacent link 156 in a particular relative orientation such that arm 54 and surgical assembly 20 support an instrument in a position relative to a surgical site, according to the requirements of a particular application. Prior to interlocking fixation, link 156 is movable relative to an adjacent link 156 through an angle in a single plane only to provide reliability in operation and fixation of mating parts, similar to that described above. It is contemplated that the barrel shaped articulation of links 156 can also provide a full hinge motion in one plane and a limited hinge motion in a plane normal to the full hinge motion in one plane.

In one embodiment, as shown in FIGS. 12-15, arm 54 of surgical assembly 20, similar to that described above, includes a series of relatively movable links 256. Link 256 has a first end 280 having a cylindrical configuration and a second end 282 having a block configuration. Links 256 define an axial bore 258 configured for disposal of cable 30. Axial bore 258 is formed with each link 256 and has a rectangular configuration therethrough that decreases in width from first end 280 to second end 282. First end 280 defines a first mating surface 260 and second end 282 defines an opposing second mating surface 262, the mating surfaces being configured to interlock with a reciprocal mating surface of an adjacent link 256 in the series of links for support and positioning of an instrument, as described above. Axial bore 258 extends through mating surfaces 260,262 for disposal of cable 30.

Mating surfaces 260,262 include a plurality of teeth 272,274 and adjacent grooves disposed arcuately about the cylindrical surface that interlock, similar to that described above. As the tension of cable 30 is increased, first mating surface 260 interlocks with second mating surface 262 of an adjacent link 256 in the series to selectively fix links 256 in a selected orientation. Teeth 272, 274 become disposed in the grooves of the opposing mating surface to selectively fix a link 256 and an adjacent link 256 in a particular relative orientation such that arm 54 and surgical assembly 20 support an instrument in a position relative to a surgical site, according to the requirements of a particular application. Prior to interlocking fixation, link 256 is movable relative to an adjacent link 256 through an angle in a single plane only to provide reliability in operation and fixation of mating parts, similar to that described above.

Figure 16:
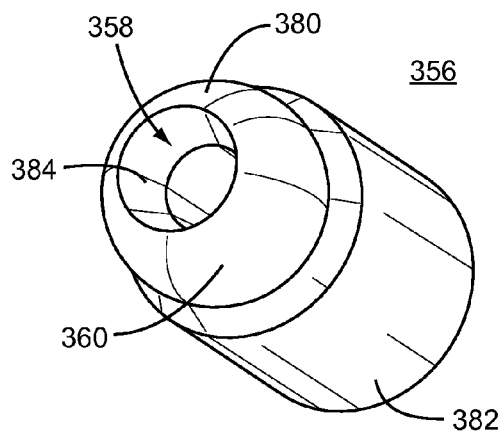
FIG. 16 is a perspective view of one embodiment of the link shown in FIG. 4.
Figure 17:
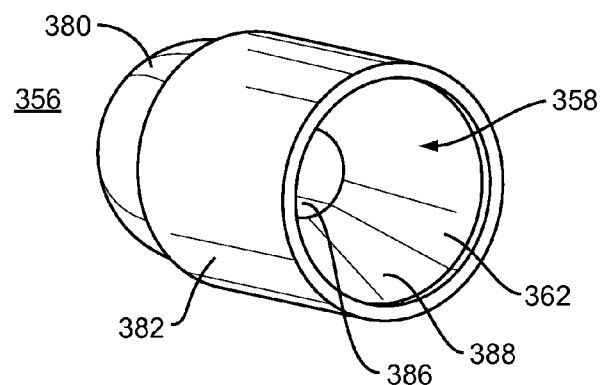
FIG. 17 is a perspective view of the link shown in FIG. 16.
Figure 18:
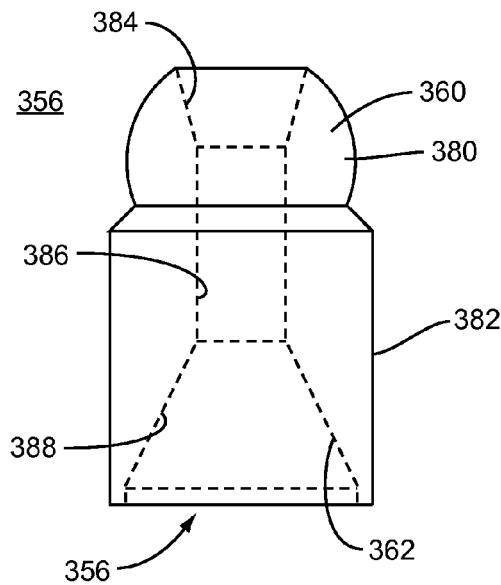
FIG. 18 is a side, cross section view of the link shown in FIG. 16.

In one embodiment, as shown in FIGS. 16-18, arm 54 of surgical assembly 20, similar to that described above, includes a series of relatively movable links 356. Link 356 has a first end 380 having a spherical dome configuration and a second end 382 having a cylindrical configuration. Links 356 define an axial bore 358 configured for disposal of cable 30. Each link 356 defines a first frustro-conical cavity 384, a cylindrical cavity 386 and a second frustro-conical cavity 388. Cavities 384,386,388 form a portion of axial bore 358 passing through each link 356 and support cable 30. This configuration provides spherical dome articulation at first end 360 and a conical socket for receiving the spherical dome of first end 360 at second end 382. Cavity 388 has a relatively larger dimension that cavity 384 to accommodate first end 360. Link 356 provides full multi-axial motion relative to an adjacent link 356 and greater locking strength upon fixation of arm 54, as described above.

First end 380 defines a first mating surface 360 and second end 382 defines an opposing second mating surface 362, the mating surfaces being configured to interlock with a reciprocal mating surface of an adjacent link 356 in the series of links for support and positioning of an instrument, as described above. Axial bore 358 extends through mating surfaces 360,362 for disposal of cable 30.

As the tension of cable 30 is increased, first mating surface 360 interlocks with second mating surface 362 of an adjacent link 356 in the series to selectively fix links 356 in a selected orientation. First mating surface 360 engages an opposing second mating surface 362 in a pressure and/or friction fit as links 356 are pulled together to selectively fix a link 356 and an adjacent link 356 in a particular relative orientation such that arm 54 and surgical assembly 20 support an instrument in a position relative to a surgical site, according to the requirements of a particular application.

Figure 19:
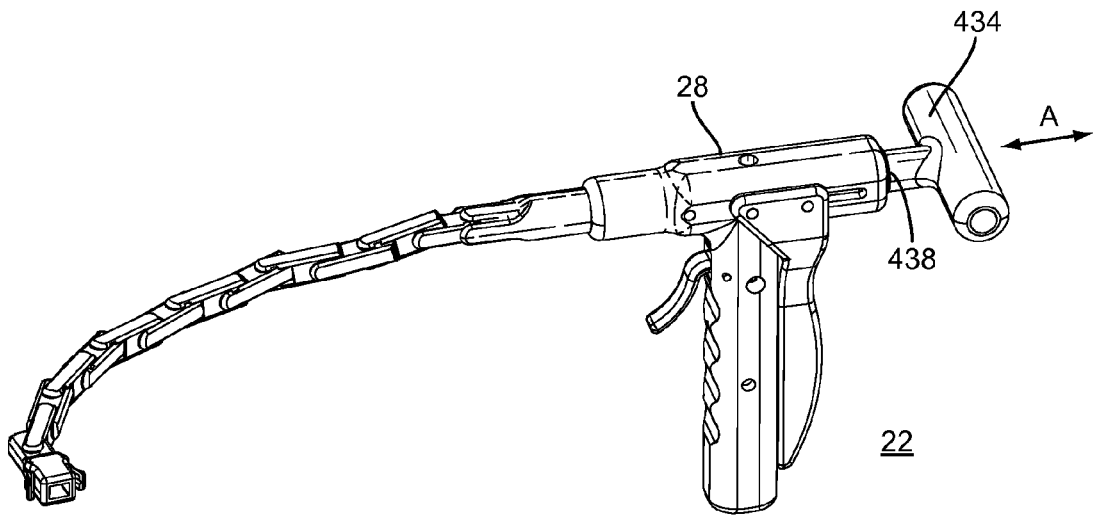
FIG. 19 is a perspective view of one embodiment of the tensioner shown in FIG. 2.

In one embodiment, as shown in FIG. 19, tensioner 22, similar to that described above, includes a first member, such as, for example, a t-handle 434. T-handle 434 is connected to body 28 and extends into body 28 through a slot 438. T-handle 434 is manipulable for tensioning cable 30, similar to slide 34 described above. T-handle 434 is axially movable, in the direction shown by arrows A through slot 438.

T-handle 434 includes an internal member (not shown) extending axially along the interior cavity of body 28 to engage a proximal end of the interlocking links. As the internal member of t-handle 434 engages the proximal end of the interlocking links, the proximal end of the interlocking links are urged/forced in the direction of arrows A according to the manipulation of t-handle 434. This engagement increases or decreases, depending on the direction of manipulation of t-handle 434 along arrows A, the tension of cable 30 due to the connection of cable 30 with body 28 and the distal end of the interlocking links, as described above. It is envisioned that t-handle 434 may include an internal member that is threaded with the interior cavity of body 28 such that t-handle 434 is rotatable or can be twisted for axial translation thereof and engagement with the proximal end of the links. In one embodiment, tensioner 22 has a first member, which includes slide 34 and t-handle 434, as shown in FIG. 19, for tensioning cable 30, as described above. For example, slide 34 may be employed to apply tension and t-handle 434 is used to provide fine adjustment.

Figure 20:
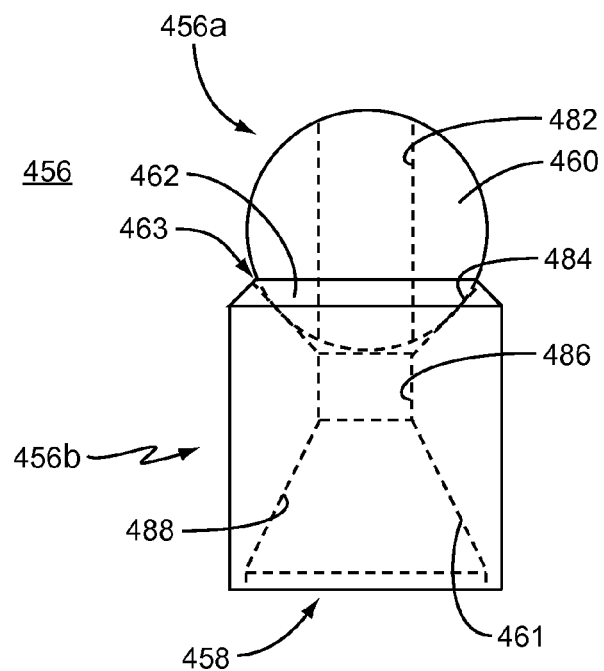
FIG. 20 is a side, cross section view of one embodiment of the links shown in FIG. 3.

In one embodiment, as shown in FIG. 20, arm 54 of surgical assembly 20, similar to that described above, includes a series of relatively movable links 456, which include a cannulated ball link 456*a* that is movable relative to a cylinder link 456*b*. Link 456*a* has a spherical configuration and link 456*b* has an elongated cylindrical configuration. Links 456 define an axial bore 458 configured for disposal of cable 30. Link 456*a* defines a cylindrical cavity 482. Link 456*b* defines a first frustro-conical cavity 484, a cylindrical cavity portion 486 and a second frustro-conical cavity 488. Cavities 482, 484,486,488 form a portion of axial bore 458 passing through links 456 and support cable 30. This configuration provides arcuate articulation cannulated ball link 456*a* and conical sockets, cavities 484, 488 for receiving link 456*a*.

Link 456*a* defines a mating surface 460 configured to interlock with a reciprocal mating surface 461 of link 456*b* and an opposing mating surface 462 configured to interlock with a reciprocal mating surface 463 of link 456*b*, in the series of links 456 for support and positioning of an instrument, as described above. Axial bore 458 extends through mating surfaces 460, 461, 462, 463 for disposal of cable 30.

As the tension of cable 30 is increased, mating surface 460 interlocks with mating surface 461 and mating surface 462 interlocks with mating surface 463 in the series to selectively fix links 456 in a selected orientation. The mating surfaces of links 456 engage in a pressure and/or friction fit as links 456 are pulled together to selectively fix a 456*a* and an adjacent link 456*b* in a particular relative orientation such that arm 54 and surgical assembly 20 support an instrument in a position relative to a surgical site, according to the requirements of a particular application.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical assembly comprising:
a tensioner having a first end and a second end, the tensioner including a body and a first member relatively movable therefrom, the first member being connected to the body and configured for manipulation for tensioning the tension member, the first member having a T-handle configuration and a ratchet mechanism connected with the body and the first member, the body being selectively fixable with the ratchet mechanism;
a tension member defining a longitudinal axis, the tension member extending from the first end of the tensioner;
a mounting member having a proximal end and a distal end, the proximal end connected to the second end of the tensioner and the distal end connected to an adjustable clamp configured for mounting with a fixture; and
an arm extending from the first end of the tensioner and including a series of relatively moveable links that define an axial bore configured for disposal of the tension member, wherein a proximal link of the links is rotatable relative to the body about the longitudinal axis and each link defines a first mating surface and a second mating surface disposed in a configuration such that tensioning of the tension member interlocks the first mating surface with the second mating surface of an adjacent link in the series to selectively fix the links in a selected orientation, each link includes a pin and a slot in communication with an axial channel configured for moveable disposal of the pin of an adjacent link, the axial channel is configured for disposal of the pin between a first freely moveable position and a second releasably fixed position, wherein the pin of one of the links extends transverse to a pin of an adjacent one of the links.

2. A surgical assembly according to claim 1, wherein the tensioner further includes a second member connected with the ratchet mechanism and being configured for manipulation to fix and release the body with the ratchet mechanism.

3. A surgical assembly according to claim 1, wherein the first mating surface of each link has a convex configuration and the second mating surface has a concave configuration.

4. A surgical assembly according to claim 1, wherein the first mating surface of each link includes a plurality of teeth configured to interlock with a plurality of teeth of the second mating surface.

5. A surgical assembly according to claim 1, wherein the axial bore of each link extends through the first mating surface and the second mating surface of each link.

6. A surgical assembly according to claim 1, wherein the first mating surface of each link is elongated along a first axis and the first mating surface of an adjacent link is elongated along a second axis, the first axis being orientated transverse to the second axis.

7. A surgical assembly according to claim 1, wherein each link is movable relative to an adjacent link through an angular range in a single plane only.

8. A surgical assembly according to claim 7, wherein the angular range is 90 degrees.

9. A surgical assembly according to claim 1, wherein the series of relatively movable links include a proximal link having a first end including a mating surface configured to interlock with the first mating surface and a second end mounted with the tensioner.

10. A surgical assembly according to claim 1, wherein the series of relatively movable links include a distal link having a mating surface configured to interlock with the second mating surface and an end for releasably engaging an instrument.

11. A surgical assembly according to claim 10, wherein the end of the distal link defines a cavity for receiving the instrument and at least one pawl for releasably retaining the instrument within the cavity.

12. A surgical assembly according to claim 1, wherein each link includes a first end having a barrel configuration with an outer surface including the first mating surface.

13. A surgical assembly according to claim 1, wherein each link includes a first end and a second end, the first end having a cylindrical configuration with an outer surface including the first mating surface, the second end having a block configuration with an outer surface including the second mating surface.

14. A surgical assembly according to claim 1, wherein each link includes a first end and a second end, the first end having a spherical configuration with an outer surface including the first mating surface and a frustro-conical inner surface, the second end having a cylindrical configuration with an inner surface including the second mating surface that is frustro-conical.

15. A surgical assembly comprising:
a tensioner having a first end, a second end, the tensioner including a body and a T-handle movably connected with the body, the body having a pistol grip configuration, the second end defining finger grips configured to handle and manipulate the tensioner;
a cable defining a longitudinal axis and including a first portion connected to the body and a second portion extending from the first end of the tensioner;
a mounting member having a proximal end and a distal end, the proximal end connected with the body of the tensioner and the distal end connected to an adjustable clamp configured for mounting with a fixture; and
an arm including a series of relatively movable links that define an axial bore configured for disposal of the cable, wherein a proximal link of the links is rotatable relative to the body about the longitudinal axis and each link defines a first mating surface and an opposing second mating surface, the mating surfaces including interlocking teeth disposed in a configuration such that engagement of the T-handle relative to the body selectively tensions the cable via engagement of the links and the first mating surface interlocks with the second mating surface of an adjacent link in the series to selectively fix the links in a selected orientation, each link includes a pin and a slot in communication with an axial channel configured for moveable disposal of the pin of an adjacent link the axial channel is configured for disposal of the pin between a first freely moveable position and a second releasably fixed position, wherein the pin of one of the links extends transverse to a pin of an adjacent one of the links.

16. A surgical assembly according to claim 1, wherein the links include a cannulated ball link that is movable relative to an adjacent link configured as a cylindrical link, the ball link defining a mating surface configured to interlock with a frustro conical mating surface of the cylindrical link.

17. A surgical assembly comprising:
a pistol-grip tensioner having a body, a slide connected to the body, and a ratchet mechanism connecting the body with the slide;
a cable defining a longitudinal axis and including a first portion connected to the body and a second portion extending from a first end of a tensioner;
a mounting member having a proximal end and a distal end, the proximal end connected with the body and the distal end connected to an adjustable clamp configured for mounting with a fixture;
a proximal link having a first end including a mating surface and a second end mounted with the body;
a series of relatively movable links that define a central axial bore having the cable disposed therein, wherein a proximal link of the links is rotatable relative to the body about the longitudinal axis and each link defines a first mating surface and a second mating surface, each link being movable relative to an adjacent link through an angular range in a single plane only, the mating surface of the proximal link configured to interlock with the first mating surface, each of the series of links includes a pin and a slot in communication with an axial channel configured for moveable disposal of the pin of an adjacent link, the axial channel is configured for disposal of the pin between a first freely moveable position and a second releasably fixed position, wherein the pin of one of the links extends transverse to a pin of an adjacent one of the links; and
a distal link having a mating surface configured to interlock with the second mating surface of an adjacent link of one of the series of links and an end for releasably engaging an instrument, wherein engagement of the slide relative to the body selectively tensions the cable via engagement of the links and the first mating surface interlocks with the second mating surface of an adjacent link in the series to selectively fix the links in a selected orientation via fixation of the ratchet mechanism with the body.

18. A surgical assembly according to claim 1, wherein the slot is disposed transverse to the axial channel.

19. A surgical assembly according to claim 1, wherein each link includes a pair of extensions that includes the slot and the axial channel.

20. A surgical assembly according to claim 1, wherein the tension member is elastic.

* * * * *

UNITED STATES PATENT AND TRADEMARK OFFICE
CERTIFICATE OF CORRECTION

PATENT NO.        : 9,486,296 B2
APPLICATION NO.   : 12/832598
DATED             : November 8, 2016
INVENTOR(S)       : Mire et al.

It is certified that error appears in the above-identified patent and that said Letters Patent is hereby corrected as shown below:

In the Specification

In Column 4, Line 38, delete "first end 31" and insert -- first end 24 --, therefor.

In Column 9, Line 5, delete "first end 360" and insert -- first end 380 --, therefor.

In Column 9, Line 6, delete "first end 360" and insert -- first end 380 --, therefor.

In Column 9, Line 8, delete "first end 360." and insert -- first end 380. --, therefor.

In Column 10, Line 16, delete "456a" and insert -- link 456a --, therefor.

Signed and Sealed this
Thirty-first Day of January, 2017

Michelle K. Lee
*Director of the United States Patent and Trademark Office*